(12) United States Patent
Mosbacher et al.

(10) Patent No.: US 8,497,409 B2
(45) Date of Patent: Jul. 30, 2013

(54) ABSORBENT ARTICLE HAVING AN OLFACTORY WETNESS SIGNAL

(75) Inventors: Richard D. Mosbacher, Neenah, WI (US); Andrew Mark Long, Appleton, WI (US); Kelly Branham, Woodstock, GA (US); Jessica Sara Van Handel, Menasha, WI (US); Darold D. Tippey, Brunswick, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 996 days.

(21) Appl. No.: 12/040,338

(22) Filed: Feb. 29, 2008

(65) Prior Publication Data

US 2009/0221980 A1    Sep. 3, 2009

(51) Int. Cl.
*A61F 13/42* (2006.01)
(52) U.S. Cl.
USPC ............... 604/361; 604/385.01; 604/358
(58) Field of Classification Search
USPC ................ 604/359–361, 364, 367
See application file for complete search history.

(56) References Cited

U.S. PATENT DOCUMENTS

| | | | |
|---|---|---|---|
| 3,971,852 A * | 7/1976 | Brenner et al. | 426/103 |
| 4,100,324 A | 7/1978 | Anderson et al. | |
| 4,704,116 A | 11/1987 | Enloe | |
| 4,940,464 A | 7/1990 | Van Gompel | |
| 5,108,385 A * | 4/1992 | Snyder | 604/397 |
| 5,284,703 A | 2/1994 | Everhart et al. | |
| 5,350,624 A | 9/1994 | Georger et al. | |
| 5,384,186 A | 1/1995 | Trinh | |
| 5,429,628 A * | 7/1995 | Trinh et al. | 604/359 |
| 5,486,166 A | 1/1996 | Bishop et al. | |
| 5,490,846 A | 2/1996 | Ellis et al. | |
| 5,552,378 A | 9/1996 | Trinh et al. | |
| 5,733,272 A * | 3/1998 | Brunner et al. | 604/359 |
| 5,749,924 A * | 5/1998 | Murch et al. | 8/137 |
| 5,766,389 A | 6/1998 | Brandon et al. | |
| 5,820,973 A | 10/1998 | Dodge, II et al. | |
| 6,063,632 A * | 5/2000 | Perkins | 436/3 |

(Continued)

FOREIGN PATENT DOCUMENTS

EP    997125 A1    5/2000
JP    51127850    11/1976

(Continued)

OTHER PUBLICATIONS

Translation Detailed Description section of JP 10-085255.*

(Continued)

*Primary Examiner* — Susan Su
(74) *Attorney, Agent, or Firm* — Dority & Manning, P.A.

(57) ABSTRACT

Absorbent articles incorporating a wetness sensor for indicating the presence of a body fluid are disclosed. The wetness sensor includes an olfactory signaling device that produces a scent or odor when a body fluid is detected. For instance, in one embodiment, an odorous composition can be contained in a water degradable pouch that releases the odorous composition when contacted with moisture. Once released, the odorous composition can produce a desired scent. In other embodiments, the odorous composition can be encapsulated within a water degradable material or can be coated on a substrate. The scent or odor that is released by the odorous composition can vary depending upon the particular application. The scent, for instance, may be pleasant or unpleasant. In one embodiment, the olfactory signaling device may be used to assist in toilet training a child.

20 Claims, 5 Drawing Sheets

U.S. PATENT DOCUMENTS

| | | | |
|---|---|---|---|
| 6,506,958 B2 | 1/2003 | Williams | |
| 6,583,722 B2 | 6/2003 | Jeutter et al. | |
| 6,596,298 B2 | 7/2003 | Leung et al. | |
| 6,603,403 B2 | 8/2003 | Jeutter et al. | |
| 6,645,190 B1 | 11/2003 | Olson et al. | |
| 6,776,287 B1 | 8/2004 | Hinde et al. | |
| 6,884,238 B2 | 4/2005 | Underhill et al. | |
| 6,932,800 B2 | 8/2005 | LaVon et al. | |
| 6,933,421 B2 | 8/2005 | Topolkaraev et al. | |
| 6,949,089 B2 | 9/2005 | Olson et al. | |
| 7,025,983 B2 | 4/2006 | Leung et al. | |
| 7,208,464 B2 | 4/2007 | Heltovics et al. | |
| 7,234,648 B2 * | 6/2007 | Tepper et al. ............ | 239/53 |
| 7,235,261 B2 | 6/2007 | Smith et al. | |
| 7,294,612 B2 | 11/2007 | Popplewell | |
| 7,306,812 B2 | 12/2007 | Zhang | |
| 2004/0082928 A1* | 4/2004 | Pesce et al. ............ | 604/361 |
| 2004/0241333 A1* | 12/2004 | Cielenski et al. ......... | 427/421.1 |
| 2005/0065489 A1 | 3/2005 | Driskell et al. | |
| 2005/0177120 A1 | 8/2005 | Olson et al. | |
| 2005/0222546 A1 | 10/2005 | Vargo et al. | |
| 2006/0229577 A1 | 10/2006 | Roe et al. | |
| 2007/0213412 A1 | 9/2007 | Bacon et al. | |
| 2008/0208151 A1* | 8/2008 | Zacharias et al. ........... | 604/361 |

FOREIGN PATENT DOCUMENTS

| | | |
|---|---|---|
| JP | 10-085255 | 4/1998 |
| JP | 12-093456 A | 4/2000 |
| JP | 2000093456 A * | 4/2000 |
| JP | 2002369838 | 12/2002 |
| JP | 2004222868 | 8/2004 |
| JP | 200768221 | 10/2007 |
| KR | 10-2000-0069529 | 11/2000 |
| KR | 10-2006-0068819 | 6/2006 |
| WO | WO 9826808 A2 * | 6/1998 |
| WO | WO 0037009 A2 | 6/2000 |
| WO | WO 2005030084 A2 | 4/2005 |
| WO | WO 2005097026 A1 | 10/2005 |

OTHER PUBLICATIONS

Translation Detailed Description section of JP 2000-093456.*
Derwent Abstract and Clipped drawing of KR 2006068819.*
Definitions of "stink", "capsule" and "encapsulate", Webster's Third New International Dictionary, unabridged.*
Translation Detailed Description section of JP 10-085255, Apr. 7, 1998.*
Translation Detailed Description section of JP 2000-093456, Apr. 4, 2000.*
Derwent Abstract and Clipped drawing of KR 2006068819, Jun. 21, 2006.*
Definitions of "stink", "capsule" and "encapsulate", Webster's Third New International Dictionary, unabridged, printed Aug. 24, 2010.*
International Search Report PCT/IB2009/050132, dated Aug. 12, 2009.
Supplementary European Search Report EP 09715005, dated Nov. 13, 2012.

* cited by examiner

ABSORBENT ARTICLE HAVING AN OLFACTORY WETNESS SIGNAL

BACKGROUND

Absorbent articles such as diapers, training pants, incontinence products, feminine hygiene products, swim undergarments, and the like conventionally include a liquid permeable body-side liner, a liquid impermeable outer cover, and an absorbent core. The absorbent core is typically located in between the outer cover and the liner for taking in and retaining liquids (e.g., urine) exuded by the wearer.

The absorbent core can be made of, for instance, superabsorbent particles. Many absorbent particles, especially those sold under the tradename HUGGIES by the Kimberly-Clark Corporation, are so efficient at absorbing liquids that it is sometimes difficult to tell whether or not the absorbent article has been insulted with a body fluid.

Accordingly, various types of moisture or wetness indicators have been suggested for use in absorbent articles. The wetness indicators may include alarm devices that are designed to assist parents or attendants identify a wet diaper condition early on. The devices produce either a visual or an audible signal.

For example, past wetness indicators have typically required incorporating open electrical circuits into the absorbent articles. For instance, two strips of conductive threads or foils have been placed in the absorbent articles and placed in communication with a power supply. The conductive threads or foils serve as conductive leads for a signaling device and form an open circuit in the article that can be closed when a body fluid, such as urine, is present in the article. Although such wetness indicators have been found to perform adequately, incorporating the wetness indicators into an absorbent article has been somewhat problematic. The wetness indicators can also add significant cost to the article.

In this regard, the present disclosure is directed to an improved wetness cue to the wearer and/or caregiver for absorbent articles that does not require an electrical circuit.

SUMMARY

In general, the present disclosure is directed to an improved wetness indicator for absorbent articles. More particularly, the wetness indicator of the present disclosure emits an olfactory signal when a liquid, such as urine, is present in the article. The wetness indicator, for instance, can emit a pleasant odor or an unpleasant odor that indicates to the wearer or to a caregiver that the absorbent article has been insulted with a body fluid. Of particular advantage, the wetness indicator, especially when emitting an unpleasant odor, can be used to assist in toilet training small children.

In one embodiment, the present disclosure is directed to an absorbent article comprising a chassis including an outer cover having an interior surface and an exterior surface. An absorbent structure is positioned adjacent to the interior surface of the outer cover. If desired, a liquid permeable body-side liner may also be incorporated into the chassis on the opposite side of the absorbent structure, such that the absorbent structure is positioned in between the outer cover and the body-side liner. The chassis may include a crotch region positioned in between a front region and a back region. The front region and the back region may define a waist region therebetween.

In accordance with one embodiment of the present disclosure, a malodorous composition may be contained in the chassis. The malodorous composition can be configured to emit relatively no appreciable odors when dry. The malodorous composition, however, can be configured to emit an unpleasant odor when wetted, such as when contacted with urine.

As used herein, a malodorous composition can comprise any composition that emits an odor that would be unpleasant to either the wearer of the absorbent article or to a caregiver. In this regard, the unpleasant odor does not have to be repulsive but can simply be a slight irritant. For example, in one embodiment, the malodorous composition may contain menthol. Menthol emits a mint-like scent that may be considered unpleasant and is typically associated with cold medications.

In an alternative embodiment, the malodorous composition may comprise an amine, a ketone, an aldehyde, a terpene, a terpenoid, an essential oil, an ester, a sulfurous compound or mixtures thereof.

In one embodiment, the malodorous composition may comprise an odiferous compound that may have a pleasant smell at low concentrations but may be unpleasant at higher concentrations. For example, fruit smells at higher concentrations can be unpleasant to the wearer.

The malodorous composition in general can comprise any suitable composition capable of emitting an unpleasant odor. The malodorous composition, for instance, can be particularly designed to release a certain scent. For instance, in one embodiment, the malodorous composition can be configured to emit a vegetable-like scent which may be considered unpleasant to small children. The scent, for instance, may smell like an onion or any other suitable vegetable.

As described above, the malodorous composition is contained in the absorbent article such that only odors are emitted when the article is wetted. For instance, in one embodiment, the malodorous composition may be encapsulated in a material that releases the malodorous composition when contacted with moisture. The encapsulating material, for instance, may be water dissolvable, water dispersible, or may otherwise degrade when contacted with moisture.

The malodorous composition may be positioned at any suitable location within the chassis as long as the composition contacts moisture when the absorbent article is wetted by a wearer. In one embodiment, for instance, the malodorous composition may be uniformly mixed with the material used to form the absorbent structure. Alternatively, the malodorous composition may be separate from the absorbent structure within the chassis. In one embodiment, the malodorous composition may be contained exclusively within the crotch region of the chassis.

In an alternative embodiment, the present disclosure is directed to an absorbent article as described above that contains a wetness indicator that emits an olfactory signal when wetted. In this embodiment, the wetness indicator comprises a pouch containing an odorous composition located within the chassis of the article. The pouch is made from a material that degrades when wetted and is positioned in the chassis so as to contact liquids absorbed by the chassis. Thus, when the absorbent article is insulted by a body fluid, the pouch degrades causing the odorous composition to release an odor signal sufficient to be sensed by the wearer or a caregiver. In this embodiment, the odorous composition may emit an unpleasant odor as described above or a pleasant odor.

The pouch can be made from any suitable material capable of degrading when contacting a body fluid, such as urine. For instance, in one particular embodiment, the pouch can be made from a starch, which includes starch derivatives. Other materials that may be used to form the pouch include gelatin, caseine, pectin, agarose, agar, chitosan, carrageenan, cellulose, a cellulose derivative, polyvinyl alcohol, polyvinylpyrrolidone, povidone, guar gum, poloxamer, polyethylene glycol, polyethylene oxide, polyacrylic acid, an alginate, xanthan gum, a hydrogel, a polyurethane, or mixtures thereof.

The above materials may be used alone or in combination with other ingredients to form the pouch. For instance, in one embodiment, a plasticizer may be combined with any of the above described materials.

In one embodiment, the pouch may include a wicking strip that allows liquids to be absorbed into the interior of the pouch as the pouch degrades. The wicking strip can be made from any suitable water absorbent material. The wicking strip, for instance, may be made from a woven or nonwoven fabric or from a hydrophilic polymer.

The odorous composition contained in the pouch can vary depending upon the particular application. The odorous composition, for instance, may comprise a solid or a liquid. In one embodiment, for instance, the odorous composition may comprise an odor agent absorbed into a porous solid material. The odorous composition may comprise, for instance, an essential oil or an extract. When emitting a pleasant odor, for instance, the odor signal emitted by the odorous composition may comprise a fragrance that has a fruit-like scent, a flower-like scent, an herbal-like scent, a woodland-like scent and the like.

Of particular advantage, absorbent articles made in accordance with the present disclosure cannot only be used to signal when the article is wet, but can also be used to assist children in toilet training. For instance, in one embodiment, an absorbent article made in accordance with the present disclosure can be placed on the torso of a child. The absorbent article can contain a malodorous composition as described above that may emit an unpleasant odor when wetted. The child can be taught to urinate in a toilet as opposed to wetting the absorbent article and releasing the unpleasant odor.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
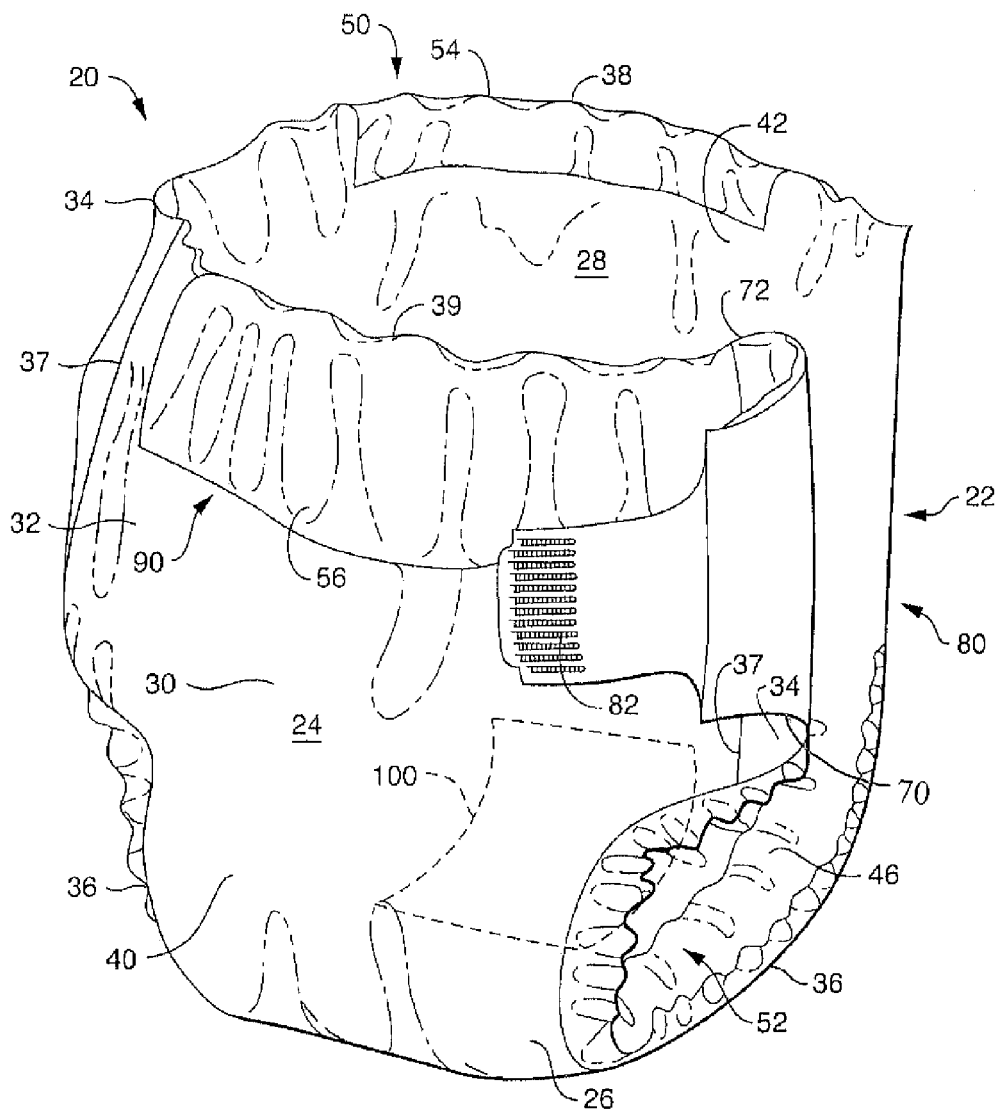
FIG. 1 is a rear perspective view of one embodiment of an absorbent article made in accordance with the present invention.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present invention.

The present disclosure is generally directed to absorbent articles containing an olfactory signaling device that is configured to indicate the presence of a body fluid in the absorbent article or other changes in the condition of the product or wearer. The absorbent article may be, for instance, a diaper, a training pant, an incontinence product, a feminine hygiene product, a medical garment, a bandage, or the like. Absorbent articles made according to the present disclosure contain an odorous composition that does not substantially emit an odor until the absorbent article is contacted with a body fluid, such as urine. For example, in one embodiment, the odorous composition may be contained in a water degradable vehicle that releases the odorous composition when wetted. Thus, once the absorbent article is wetted, the odorous composition emits an odor that indicates to the wearer or to a caregiver that a body fluid has been detected within the article.

The scent or odor that is released by the odorous composition when wetted can vary depending upon the particular application. The scent, for instance, may be pleasant to the wearer and/or the caregiver or can be unpleasant.

When incorporating an unpleasant scent into the odorous composition, it should be understood that any suitable scent may be used that would be found unpleasant either to the wearer of the absorbent article or to a caregiver. The perception of odor and its relative pleasantness, for instance, may vary by age. While some scents are universally perceived as pleasant regardless of age, perception of some odors are age dependent. Menthol, for instance, can be negatively perceived by children although some adults may consider the scent pleasant. Other scents that may be perceived as unpleasant by a child include, for instance, sage and various terpenes. Further, a scent a child may find pleasant at low concentrations, may be considered unpleasant at higher concentrations, such as various fruit smells. In this regard, in one embodiment of the present disclosure, an odorous composition can be incorporated into the article that, while unpleasant to the wearer, may not be unpleasant to the people surrounding the wearer. These circumstances may be ideal in that the article indicates to the caregiver that the article has become wetted without any significant unpleasantness, while still providing negative feedback to the child.

In one embodiment, an absorbent article made in accordance with the present disclosure can be used as a method of potty training a child. Toilet training a child, for instance, can be a challenge leading to an exhausting and slow process. In this regard, in the past, various disposable training pants have been developed that are intended to assist in the toilet training process. For example, some training pants in the past have suggested placing a visual cue on the product that indicates when the product has been wetted. For instance, various graphics have been applied to training pants that fade when the pants are insulted with urine.

Instead of a visual cue, however, the present disclosure is directed to an olfactory cue that signals to a child and caregiver that the pant has been insulted. Of particular advantage, an olfactory cue may provide a more rapid indication that the absorbent article has been wetted as opposed to various visual cues that have been suggested in the past. For instance, typically visual cues have required the child to be undressed for the caregiver to become aware that the wetting has occurred. The olfactory cue of the present disclosure transcends this limitation. The odorous composition contained in the absorbent article can be designed to release a scent that the wearer would begin to associate with the need to use the toilet. For instance, a scent may be used that is unpleasant thus encouraging the wearer to use a toilet as opposed to being subjected to the unpleasant scent. As used herein, an unpleasant scent can be any scent that is not particularly preferred by the wearer but does not necessarily have to be repulsive such that the scent would create a distraction in public.

Figure 2:
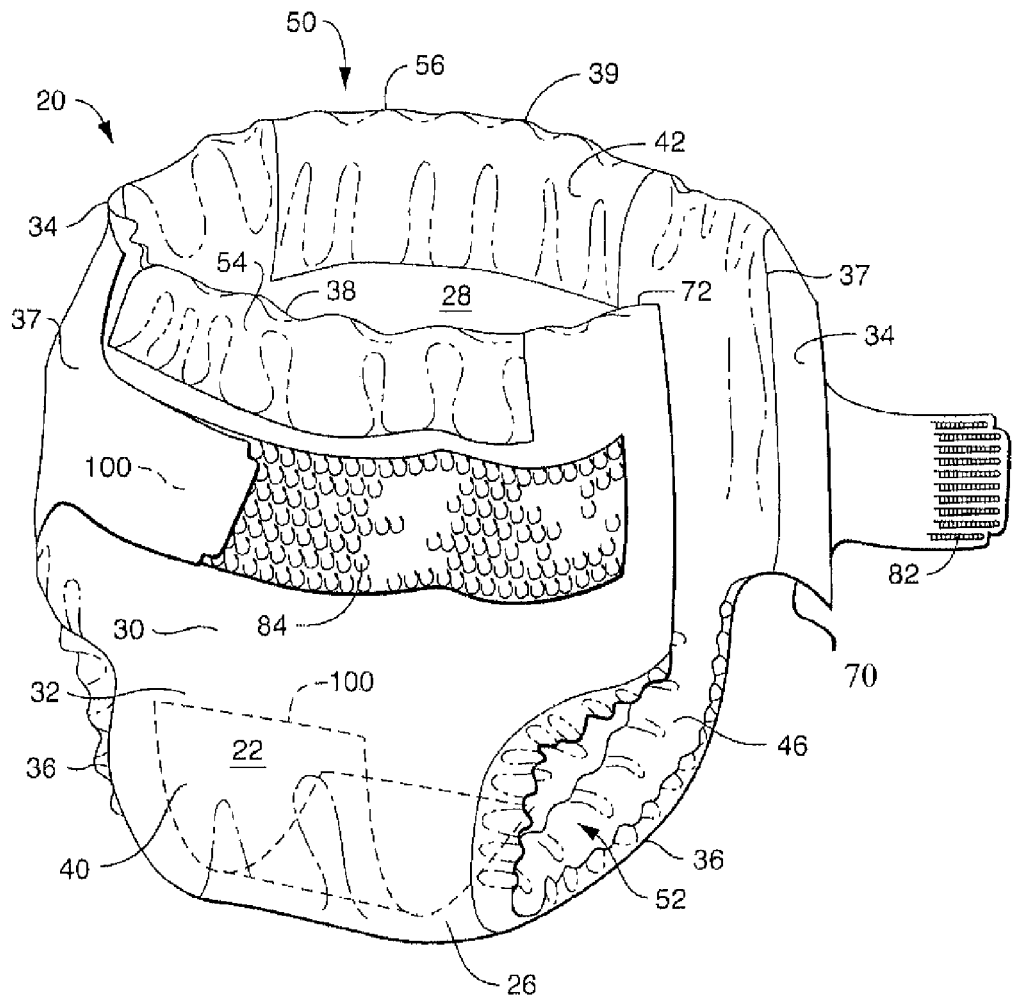
FIG. 2 is a front perspective view of the absorbent article illustrated in FIG. 1.

Referring to FIGS. 1 and 2, for exemplary purposes, an absorbent article 20 that may be made in accordance with the present disclosure is shown. The absorbent article 20 may or may not be disposable. It is understood that the present disclosure is suitable for use with various other absorbent articles intended for personal wear, including but not limited to diapers, training pants, swim pants, feminine hygiene products, incontinence products, medical garments, surgical pads and bandages, other personal care or health care garments, and the like without departing from the scope of the present invention.

By way of illustration only, various materials and methods for constructing absorbent articles such as the article 20 of the various aspects of the present invention are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
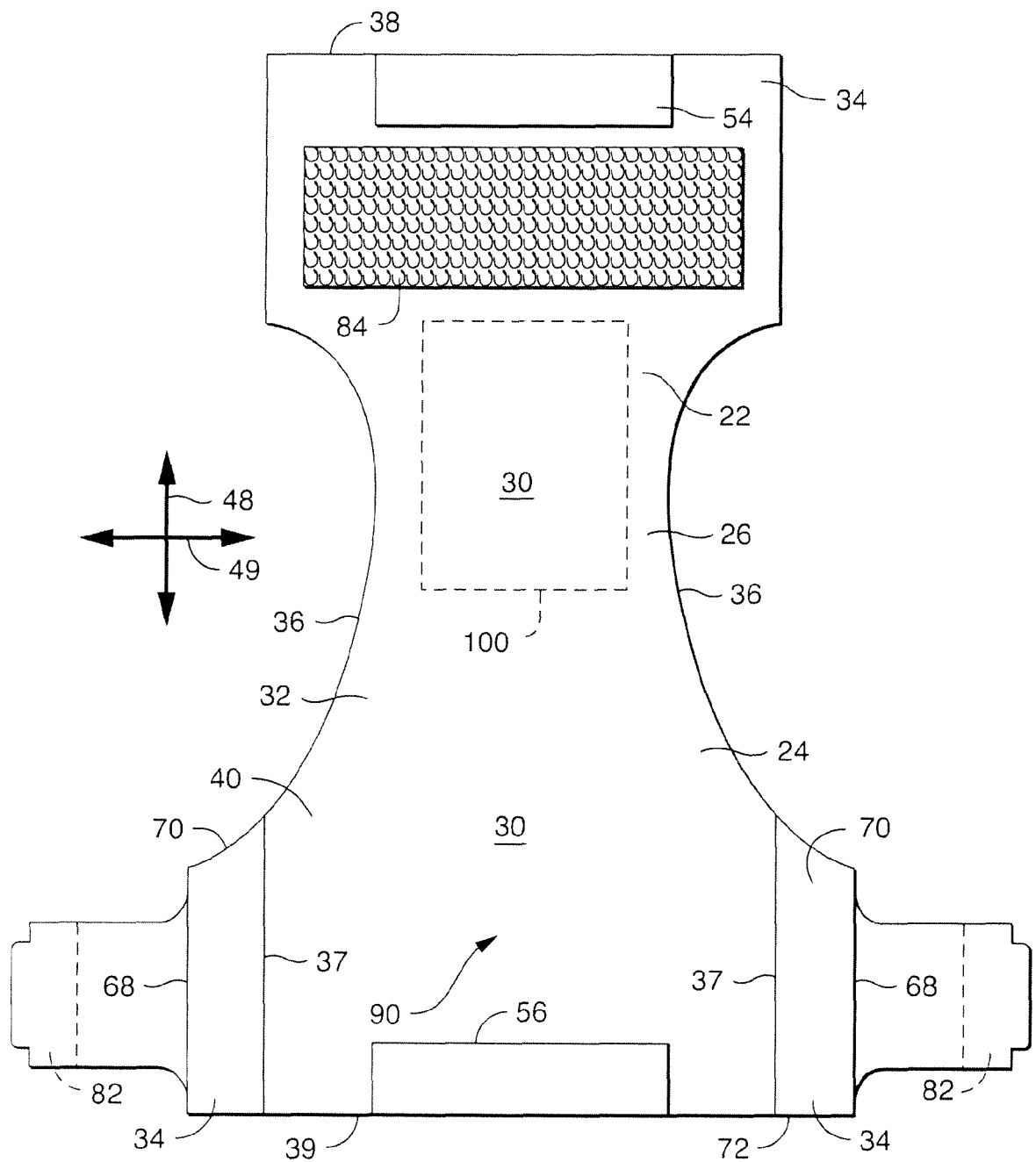
FIG. 3 is a plan view of the absorbent article shown in FIG. 1 with the article in an unfastened, unfolded and laid flat condition showing the surface of the article that faces away from the wearer.
Figure 4:
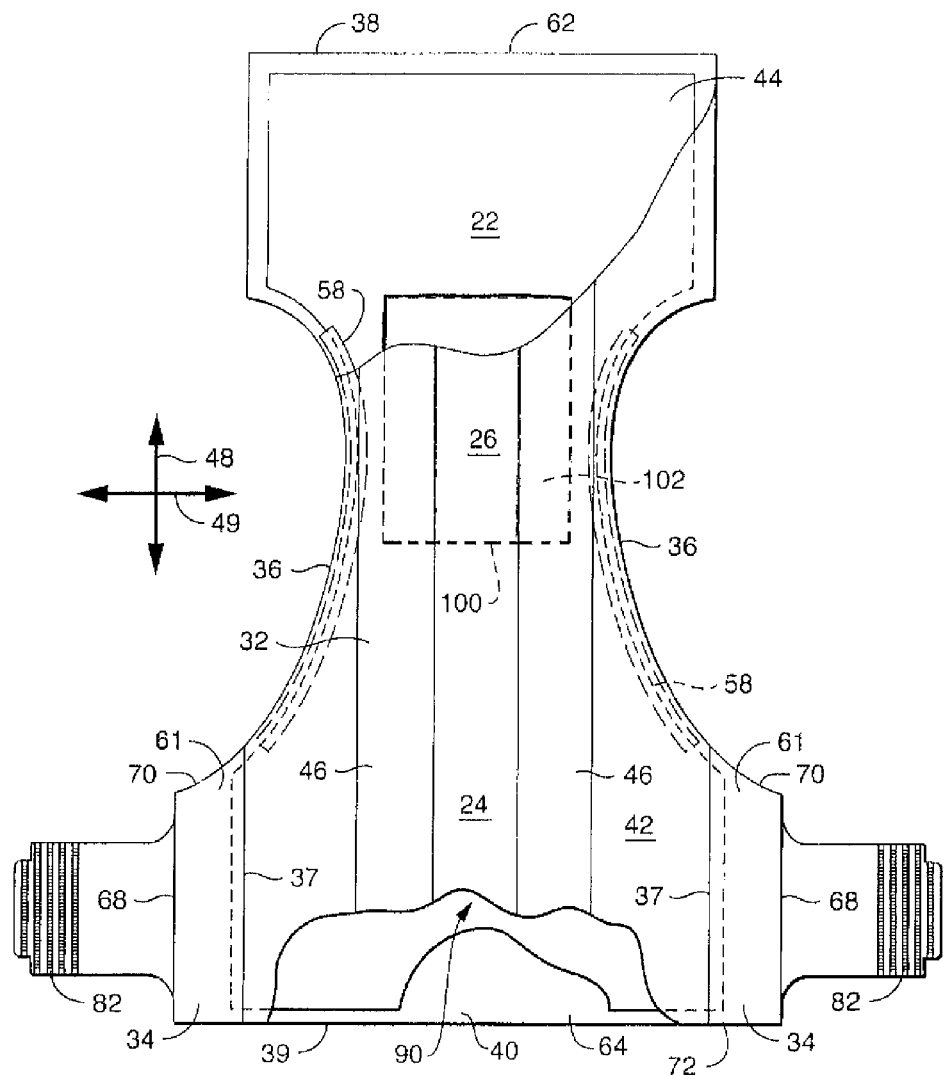
FIG. 4 is a plan view similar to FIG. 3 showing the surface of the absorbent article that faces the wearer when worn and with portions cut away to show underlying features including an olfactory signaling device.

An absorbent article 20 is representatively illustrated in FIG. 1 in a partially fastened condition. The absorbent article 20 shown in FIGS. 1 and 2 is also represented in FIGS. 3 and 4 in an opened and unfolded state. Specifically, FIG. 3 is a plan view illustrating the exterior side of the absorbent article 20, while FIG. 4 illustrates the interior side of the absorbent article 20. As shown in FIGS. 3 and 4, the absorbent article 20 defines a longitudinal direction 48 that extends from the front of the article when worn to the back of the article. Opposite to the longitudinal direction 48 is a lateral direction 49.

The absorbent article 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The absorbent article 20 also defines an inner surface 28 adapted in use (e.g., positioned relative to the other components of the article 20) to be disposed toward the wearer, and an outer surface 30 opposite the inner surface. The front and back regions 22, 24 are those portions of the absorbent article 20, which when worn, wholly or partially cover or encircle the waist or mid-lower torso of the wearer. The crotch region 26 generally is that portion of the absorbent article 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated absorbent article 20 includes a chassis 32, that, in this embodiment, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during wear of the absorbent article. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the absorbent article 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the absorbent article 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retroactive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In some embodiments, the absorbent article 20 may further include a surge management layer (not shown) which may be optionally located adjacent the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S.

Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative embodiment, the elastic side panels may also be integrally formed with the chassis 32. For instance, the side panels 34 may comprise an extension of the bodyside liner 42, of the outer cover 40, or of both the bodyside liner 42 and the outer cover 40.

In the embodiments shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a 3-dimensional diaper configuration having a waist opening 50 and a pair of leg openings 52. The waist opening 50 of the article 20 is defined by the waist edges 38 and 39 which encircle the waist of the wearer.

In the embodiments shown in the figures, the side panels are releasably attachable to the front region 22 of the article 20 by the fastening system. It should be understood, however, that in other embodiments the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the absorbent article 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. As shown in FIG. 4, the outer edges 68 are generally parallel to the longitudinal direction 48 while the waist end edges 72 are generally parallel to the transverse axis 49. It should be understood, however, that in other embodiments the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the embodiment shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material; or the like. One skilled in the art will recognize that the shape, density and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the embodiment shown in the figures, the fastening components 82 are attached to the side panels 34 along the edges 68. In this embodiment, the fastening components 82 are not elastic or extendable. In other embodiments, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

As described above, the present disclosure is particularly directed to incorporating an olfactory signaling device into the absorbent article 20. In particular, the olfactory signaling device is configured to release a scent or odor when wetted with a body fluid, such as urine. In one embodiment, for instance, the olfactory signaling device may comprise a water degradable pouch 100 as shown in FIG. 4. In accordance with the present disclosure, the pouch 100 contains an odorous composition. The pouch is configured to release the odorous composition when wet thus creating a scent or odor detectable by the wearer and/or a caregiver.

The pouch 100, for instance, can be made from any suitable material capable of releasing the odorous composition when wetted. For instance, the pouch can be made from a material that completely or partially dissolves when wetted, that is water dispersible, or that otherwise degrades in the presence of moisture.

At least one portion of the pouch 100, for instance, in one embodiment, can be made from a hydrophilic polymer or other material that dissolves or disintegrates when contacted with water. Such materials include but are not limited to protein-based materials such as gelatin or caseine, pectin, agarose, agar, chitosan, carrageenan, starch including starch derivatives, cellulose, cellulose derivates including methylcellulose, carboxymethylcellulose such as calcium carboxymethylcellulose or sodium carboxymethylcellulose, a crosslinked polymer of sodium carboxymethylcellulose, microcrystalline cellulose, ethylcellulose, hydroxyethylcellulose, hydroxypropylcellulose, hydroxypropylmethylcellulose, hydroxypropylmethylcellulose phthalate, other cellulose ethers, cellulose acetate, or cellulose acetate phthalate. Other materials include polyvinyl alcohol, polyvinylpyrrolidone, cross-linked povidone, guar gum, poloxamer, polyethylene glycol, polyethylene oxide, polyacrylic acid, an alginate such as sodium alginate, xanthan gum, hydrogels, pullulan, tragacanth gum, acacia gum, arabic gum, methylmethacrylate copolymer, carboxyvinyl polymer, amylose, dextrin, chitin, levan, elsinan, collagen, zein, gluten, polyurethane, and mixtures thereof.

When using the above materials to form all or a portion of the pouch, the above materials can be combined with various other ingredients. For instance, in one embodiment, a plasticizer may be present. Examples of plasticizers include, but are not limited to, glycerin, propylene glycol, polyethylene glycol, polypropylene glycol, sugar alcohols, and corn syrup.

In addition to plasticizers, various other ingredients may be present including fillers, colorants, compatibilizers, and the like.

The pouch 100 of the present disclosure can be positioned within the absorbent article at any suitable location. In general, the pouch should be located in the absorbent article such that the absorbent article contacts body fluids that are emitted by the wearer. As shown in FIG. 4, for instance, the pouch 100 may be placed generally in the crotch region 26 of the absorbent article 20. For instance, the pouch 100 may completely lay within the crotch region 26 or may be placed both in the crotch region 26 and the front region 22.

In FIG. 4, the pouch 100 is shown located between the bodyside liner 42 and the absorbent structure 44. It should be understood, however, that the pouch 100 can be contained in the chassis in other ways. For instance, in an alternative embodiment, the pouch 100 may be embedded within the absorbent structure 44 so that liquids collected by the absorbent structure are in continuous contact with the pouch. Alternatively, the pouch 100 may be a separate component to the absorbent article 20. In this embodiment, for instance, a consumer may have the option of incorporating the pouch into the absorbent article. The pouch, for instance, may be attached to the liner using any suitable technique. For instance, the pouch may be attached to the liner using an attachment mechanism or may fit into a pocket built into the absorbent article.

The size and shape of the pouch 100 can vary depending upon the particular application. In the embodiment shown in FIG. 4, for instance, the pouch has a rectangular shape. The pouch 100, however, may also be circular or oval. When rectangular, the pouch, for instance, may have a length and a width that vary from about 1 cm to about 12 cm. The size of the pouch may vary, for instance, on the ability of the pouch to contact liquids absorbed into the article and the type of odorous composition contained in the pouch.

Figure 5:
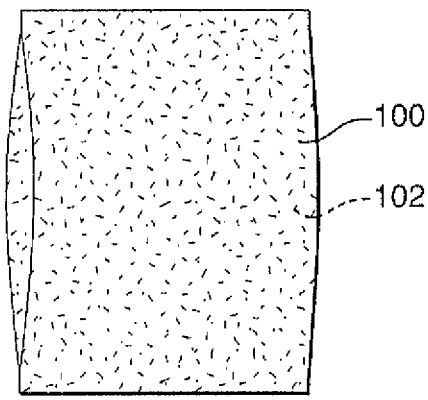
FIG. 5 is a perspective view of one embodiment of an olfactory signaling device that may be incorporated into an absorbent article and that is configured to emit an odor when wetted.
Figure 6:
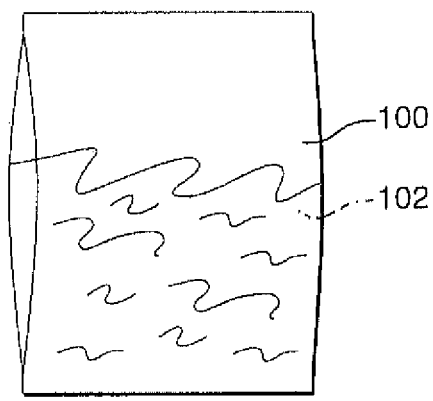
FIG. 6 is a perspective view of another embodiment of an olfactory signaling device that may be incorporated into an absorbent article and that is configured to emit an odor when wetted.
Figure 7:
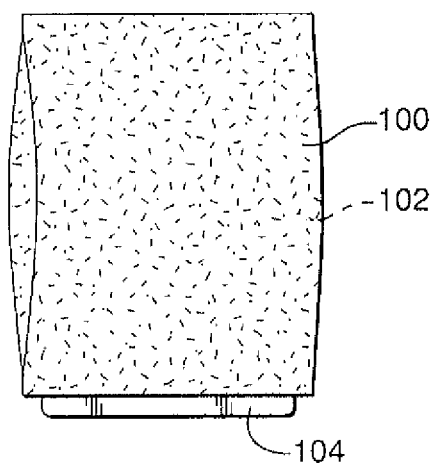
FIG. 7 is a perspective view of still another embodiment of an olfactory signaling device that may be incorporated into an absorbent article and that is configured to emit an odor when wetted.

Referring to FIGS. 5-7, various embodiments of pouches made in accordance with the present disclosure are illustrated. Like reference numerals have been used to indicate similar elements.

Referring to FIG. 5, for instance, a pouch 100 is shown containing an odorous composition 102. In this embodiment, the odorous composition 102 comprises a solid. The solid, for instance, may comprise any suitable material that produces the odor or scent. Alternatively, an oil or liquid may be incorporated into a porous solid that produces the scent or odor. The porous solid may comprise, for instance, vermiculite, or any other suitable particle.

In FIG. 6, a similar pouch 100 is shown containing an odorous composition 102. In FIG. 6, however, the odorous composition 102 comprises a liquid. The liquid may comprise, for instance, any suitable aqueous solution, essential oil, or extract capable of producing a desired scent or odor.

Referring to FIG. 7, another embodiment of a pouch 100 made in accordance with the present disclosure is shown. As illustrated, the pouch 100 includes an odorous composition 102. In this embodiment, the pouch 100 further includes a wicking strip 104. The wicking strip may be present in order to allow liquids to flow into the interior of the pouch. The wicking strip may also be used to help disintegrate or degrade the pouch 100.

The wicking strip 104 can be made from any suitable water absorbable, dissolvable, or dispersible material. In one embodiment, for instance, the wicking strip 104 may comprise a textile material, such as a woven or nonwoven web capable of absorbing liquids. Alternatively, the wicking strip 104 may comprise a dissolvable film that, once contacted with water, dissolves causing the pouch to open and to release its contents.

Various different materials can be used for the odorous composition 102. The odorous composition, for instance, may be configured to release a pleasant scent or an unpleasant scent depending upon the particular application. In general, any suitable odorous composition may be used as long as the composition is compatible with the pouch 100 and capable of releasing a scent or odor when contacted with a body fluid, such as urine.

When producing a pleasant scent, for instance, the odorous composition may produce a flower-like scent, an herbal-like scent, a fruit-like scent, or a woodland-like scent. Suitable fragrances include, for instance, almond, apple, cherry, grape, pear, pineapple, orange, strawberry, raspberry, musk, lavender, rose, iris, carnation, rosemary, thyme, sage, pine, spruce, and the like. The odorous composition may comprise, for instance, an essential oil, an extract, an aqueous solution, a solvent-based solution, and the like produced from natural or artificial sources capable of producing any suitable scent. When the odorous composition comprises a liquid, for instance, the composition can be highly volatile, by having a boiling point of less than about 250° C.

The following are examples of fragrance ingredients: extracts from natural raw materials such as essential oils, concretes, absolutes, resins, resinoids, esters, terpenes, terpenoids, balsams, tinctures such as for example, ambergris tincture; amyris oil; angelica seed oil; angelica root oil; aniseed oil; valerian oil; basil oil; tree moss absolute; bay oil; armoise oil; benzoe resinoid; bergamot oil; beeswax absolute; birch tar oil; bitter almond oil; savory oil; buchu leaf oil; cabreuva oil; cade oil; calamus oil; camphor oil; cananga oil; cardamom oil; cascarilla oil; cassia oil; cassie absolute; castoreum absolute; cedar leaf oil; cedar wood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oakmoss absolute; elemi oil; estragon oil; eucalyptus citriodora oil; eucalyptus oil (cineole type); fennel oil; fir needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; blue camomile oil; Roman camomile oil; carrot seed oil; cascarilla oil; pine needle oil;

spearmint oil; caraway oil; labdanum oil; labdanum absolute; labdanum resin; lavandin absolute; lavandin oil; lavender absolute; lavender oil; lemon-grass oil; lovage oil; lime oil distilled; lime oil expressed; linaloe oil; Litsea cubeba oil; laurel leaf oil; mace oil; marjoram oil; mandarin oil; massoi (bark) oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange flower absolute; orange oil; origanum oil; palmarosa oil; patchouli oil; perilla oil; Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; Dalmatian sage oil; Spanish sage oil; sandalwood oil; celery seed oil; spike-lavender oil; star anise oil; storax oil; tagetes oil; fir needle oil; tea tree oil; turpentine oil; thyme oil; Tolu balsam; tonka bean absolute; tuberose absolute; vanilla extract; violet leaf absolute; verbena oil; vetiver oil; juniperberry oil; wine lees oil; wormwood oil; wintergreen oil; ylang-ylang oil; hyssop oil; civet absolute; cinnamon leaf oil; cinnamon bark oil; and fractions thereof or ingredients isolated therefrom.

Other fragrances suitable for use in the present disclosure include various hydrocarbons that are configured to produce the desired scent.

As described above, in one embodiment, the odorous composition is configured to emit an unpleasant scent. The scent may be considered unpleasant, for instance, to a child and/or to a caregiver.

Unpleasant scents that may be used include, for instance, vegetable-like scents. For instance, an onion-like scent, a carrot-like scent, a garlic-like scent, and the like may be considered unpleasant to a child. In addition, pleasant scents can become unpleasant scents when present in high concentrations. For instance, fruit smells, such as the smell of a banana, can be unpleasant to a child when present in high enough concentrations.

In one embodiment, the odorous composition may comprise menthol for emitting a mint-like scent that may be considered unpleasant.

Other materials that may deliver an unpleasant scent include amines, ketones, aldehydes, terpenes, terpenoids, esters, or sulfurous compounds. Terpenes and terpenoids, for instance, are the primary constituents of essential oils of many types of plants and flowers. Odors emitted by terpenes and terpenoids may be considered pleasant or unpleasant depending upon the circumstances and the concentration. Esters are a class of chemical compounds and functional groups. Esters can be produced from inorganic or organic acids in which at least one hydroxy group is replaced by an —O-alkyl (alkoxy) group. Common esters are carboxylic acid esters ($R^1$—C(=O)—O—$R^2$). Other esters are produced from phosphoric acid, sulfuric acid, nitric acid, and boric acid. Volatile esters are used, for instance, in perfumes, essential oils, and give many fruits their scent. Examples of esters that produce odors include ethyl acetate (fruity, solvent), ethyl butanoate (fruity) also known as ethyl butyrate, ethyl decanoate also known as ethyl caprate, ethyl hexanoate also known as ethyl caproate, ethyl octanoate also known as ethyl caprylate, hexyl acetate (apple, floral, fruity), isoamyl acetate (banana), methyl butanoate (apple, fruity) also known as methyl butyrate, methyl salicylate (oil of wintergreen), pentyl butanoate (pear, apricot), pentyl pentanoate (apple, pineapple), sotolon (maple syrup, curry, fenugreek), and strawberry aldehyde (strawberry).

When containing an unpleasant scent, the olfactory signaling device of the present disclosure may be well suited to not only signaling when the absorbent article is wet, but may also assist in potty training a child. For instance, a child can be instructed and encouraged to properly use a toilet instead of wetting the absorbent article and releasing the unpleasant odor. Since the unpleasant odor will be detected by the caregiver, the caregiver is also in a position to immediately reinforce potty training when an accident occurs.

In the embodiments illustrated in the figures, the odorous composition is contained in a pouch 100. It should be understood, however, that the odorous composition may be contained in the absorbent article in various other ways. For instance, in one embodiment, the odorous composition may be encapsulated, such as microencapsulated, in a material that dissolves, disintegrates, or otherwise degrades when wetted thereby releasing the odorous composition.

Various different materials are available for encapsulating an odorous composition. For instance, many of the materials described above to form the pouch can also be used to encapsulate the odorous composition. Particular materials that may be used to encapsulate the odorous composition include, for instance, a cyclodextrin, a polysaccharide or other suitable material.

In addition to using encapsulated materials, the odor or scent delivery device may also comprise a coated substrate or an impregnated film in which an odorous composition is enveloped by a material that degrades when contacted with water.

When using the above odor delivery devices, the odorous composition can be contained throughout the chassis or contained only in a single location. In one embodiment, for instance, an encapsulated odorous composition may be combined with the material used to form the absorbent structure. Alternatively, the encapsulated material may be deposited in a large concentration only in a single area of the absorbent structure, such as within the crotch region.

Various different materials can be used to make the absorbent article. The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded card webs or foams provided by elastomeric or polymeric materials. The outer cover 40, for instance, can be a single layer of a liquid impermeable material, or alternatively can be a multi-layered laminate structure in which at least one of the layers is liquid impermeable. In other embodiments, however, it should be understood that the outer cover may be liquid permeable. In this embodiment, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded-web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., USA, and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394, and Favor 9543 superabsorbents are available from DeGussa Superabsorbers.

After being formed or cut into a desired shape, the absorbent web material may be wrapped or encompassed by a suitable tissue or meltblown web or the like wrap sheet that aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. Nos. 4,100,324 to Anderson, et al.; 5,284,703 to Everhart, et al.; and 5,350,624 to Georger, et al.; which are incorporated herein by reference to the extent they are consistent (i.e., not in conflict) herewith.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article comprising:
   a chassis comprising an outer cover having an interior surface and an exterior surface, the chassis containing an absorbent structure positioned adjacent to the interior surface of the outer cover, the chassis including a crotch region positioned in between a front region and a back region, the front region and the back region defining a waist region therebetween;
   a malodorous composition contained in the chassis, the malodorous composition being positioned in the chassis so as to contact a liquid absorbed by the absorbent structure, the malodorous composition being configured to emit an olfactory cue when the absorbent article is wetted;

wherein the malodorous composition is selected from the group consisting of menthol, an amine, a ketone, an aldehyde, an ester, a sulfurous compound, or mixtures thereof; and wherein the malodorous composition is contained in a pouch that releases the malodorous composition when wetted and the pouch includes a wicking strip configured to allow liquid to flow along the wicking strip into the interior of the pouch.

2. The absorbent article as defined in claim 1, wherein the malodorous composition is encapsulated in a material that releases the malodorous composition when wetted.

3. The absorbent article as defined in claim 1, wherein the pouch is made from a water degradable material.

4. The absorbent article as defined in claim 1, wherein the malodorous composition is only present in the crotch region of the chassis.

5. An absorbent article comprising:
a chassis comprising an outer cover having an interior surface and an exterior surface, the chassis containing an absorbent structure positioned adjacent the interior surface of the outer cover, the chassis including a crotch region positioned in between a front region and a back region, the front region and the back region defining a waist region therebetween; and
a pouch containing an odorous composition located in the chassis, the pouch being made from a material that degrades when wetted, the pouch being positioned in the chassis so as to contact liquids absorbed into the chassis when the absorbent article is being worn, wherein the pouch further comprises a wicking strip extending from the pouch that allows liquids to be absorbed into an interior of the pouch, and wherein, when wetted, the pouch degrades and the wicking strip dissolves to open the pouch to release the odorous composition causing the odorous compound to release an odor signal sufficient to be sensed by the wearer.

6. The absorbent article as defined in claim 5, wherein the material used to form the pouch comprises a starch.

7. The absorbent article as defined in claim 6, wherein the material used to form the pouch further comprises a plasticizer.

8. The absorbent article as defined in claim 5, wherein the material used to form the pouch comprises gelatin, caseine, pectin, agarose, agar, chitosan, carrageenan, cellulose, a cellulose derivative, polyvinyl alcohol, polyvinylpyrrolidone, povidone, guar gum, poloxamer, polyethylene glycol, polyethylene oxide, polyacrylic acid, an alginate, xanthan gum, a hydrogel, a polyurethane, or mixtures thereof.

9. The absorbent article as defined in claim 7, wherein the material used to form the pouch further comprises a plasticizer.

10. The absorbent article as defined in claim 5, wherein the odorous composition comprises a liquid.

11. The absorbent article as defined in claim 5, wherein the odorous composition comprises a solid.

12. The absorbent article as defined in claim 5, wherein the odorous composition emits a olfactory signal.

13. The absorbent article as defined in claim 12, wherein the odorous composition comprises menthol.

14. The absorbent article as defined in claim 12, wherein the olfactory signal has a vegetable-like scent.

15. The absorbent article as defined in claim 5, wherein the odorous composition comprises an essential oil or an extract.

16. The absorbent article as defined in claim 5, wherein the odor signal comprises a fragrance, the fragrance having a fruit-like smell, a flower-like smell, an herbal-like smell, or a woodland-like smell.

17. The absorbent article as defined in claim 5, wherein the odorous composition has a pleasant smell at low concentrations and an unpleasant smell at higher concentrations.

18. A method for toilet training a child comprising:
donning on a child an absorbent article, the absorbent article including a chassis that defines two leg openings opposite a waist opening, the chassis comprising an outer cover having an interior surface and an exterior surface, the chassis further including an absorbent structure positioned adjacent the interior surface of the outer cover, the chassis including a crotch region positioned in between the two leg openings and in between a front region and a back region of the chassis, the absorbent article further containing a malodorous composition that is configured to emit an unpleasant odor when wetted wherein the malodorous compound is selected from the group consisting of menthol or ester;
wherein the malodorous composition is contained in a pouch that releases the malodorous composition when wetted and the pouch includes a wicking strip configured to allow liquid to flow along the wicking strip into the interior of the pouch; and
instructing the child to urinate in a toilet as opposed to urinating in the absorbent article and releasing the unpleasant odor.

19. An absorbent article comprising:
a chassis comprising an outer cover having an interior surface and an exterior surface, the chassis containing an absorbent structure positioned adjacent to the interior surface of the outer cover, the chassis including a crotch region positioned in between a front region and a back region, the front region and the back region defining a waist region therebetween;
a malodorous composition contained in the chassis, the malodorous composition being positioned in the chassis so as to contact a liquid absorbed by the absorbent structure, the malodorous composition being configured to emit an olfactory cue when the absorbent article is wetted
wherein the malodorous composition is contained in a pouch that releases the malodorous composition when wetted and the pouch includes a wicking strip configured to allow liquid to flow along the wicking strip into the interior of the pouch; and
wherein the olfactory cue emitted by the malodorous composition comprises a vegetable-like scent.

20. A method for toilet training a child comprising:
donning on a child an absorbent article, the absorbent article including a chassis that defines two leg openings opposite a waist opening, the chassis comprising an outer cover having an interior surface and an exterior surface, the chassis further including an absorbent structure positioned adjacent the interior surface of the outer cover, the chassis including a crotch region positioned in between the two leg openings and in between a front region and a back region of the chassis, the absorbent article further containing a malodorous composition that is configured to emit an unpleasant vegetable-like or fruit-like scent when wetted;
wherein the malodorous composition is contained in a pouch that releases the malodorous composition when wetted and the pouch includes a wicking strip configured to allow liquid to flow along the wicking strip into the interior of the pouch; and instructing the child to urinate in a toilet as opposed to urinating in the absorbent article and releasing the unpleasant odor.

\* \* \* \* \*